US008005628B2

(12) United States Patent  
Gunstream

(10) Patent No.: US 8,005,628 B2  
(45) Date of Patent: Aug. 23, 2011

(54) SYSTEMS AND METHODS FOR BASELINE CORRECTION USING NON-LINEAR NORMALIZATION

(75) Inventor: Stephen J. Gunstream, San Francisco, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 69 days.

(21) Appl. No.: 12/022,087

(22) Filed: Jan. 29, 2008

(65) Prior Publication Data

US 2008/0182264 A1    Jul. 31, 2008

Related U.S. Application Data

(60) Provisional application No. 60/898,064, filed on Jan. 29, 2007.

(51) Int. Cl.  
*G06F 19/00* (2006.01)

(52) U.S. Cl. .......................................... 702/32

(58) Field of Classification Search .............. 702/32; 435/6, 287.1  
See application file for complete search history.

(56) References Cited

U.S. PATENT DOCUMENTS

| | | | |
|---|---|---|---|
| 5,850,623 A | 12/1998 | Carman, Jr. et al. | |
| 6,471,916 B1 | 10/2002 | Noblett | |
| 6,991,712 B2 | 1/2006 | Sharaf et al. | |
| 7,089,123 B2 | 8/2006 | Corson et al. | |
| 7,233,393 B2 * | 6/2007 | Tomaney et al. | 356/307 |
| 2006/0102479 A1 | 5/2006 | Sharaf et al. | |
| 2006/0138344 A1 | 6/2006 | Gunstream et al. | |
| 2007/0248982 A1 * | 10/2007 | Woo et al. | 435/6 |
| 2008/0133198 A1 * | 6/2008 | Carrick | 703/11 |
| 2008/0154512 A1 * | 6/2008 | Leong | 702/19 |
| 2008/0178653 A1 | 7/2008 | Gunstream | |
| 2008/0209978 A1 | 9/2008 | Gunstream | |
| 2010/0198525 A1 | 8/2010 | Gunstream | |

OTHER PUBLICATIONS

"Relative Quantification", *Roche Applied Science Technical Note No. LC13/2001* Retrieved from https://www.roche-applied-cience.com/sis/rtpcr/lightcycler/lightcycler_docs/technical_notes/lc_13.pdf on May 14, 2009, 2001.  
U.S. Appl. No. 12/022,079, "Office Action mailed Nov. 17, 2009", 7 pgs.  
U.S. Appl. No. 12/022,079, "Response to Jul. 15, 2010 Office Action", filed Nov. 15, 2010 12 pgs.  
U.S. Appl. No. 12/022,079, "Office Action mailed Jul. 15, 2010", 7 pgs.  
U.S. Appl. No. 12/543,742 Office Action dated Sep. 27, 2010, 17 pages.  
U.S. Appl. No. 12/543,742 Response to Office Action dated Sep. 27, 2010 filed Feb. 28, 2011, 8 pgs.

(Continued)

*Primary Examiner* — Bryan Bui

(57) ABSTRACT

Systems and methods for normalizing detected emission data collected in real-time polymerase chain reaction (RT-PCR) and other reactions, are provided. In some embodiments, a sample plate can be loaded with a fluorescent dye and subjected to a real-time PCR reaction. During the initial cycles, detected emissions that correspond to the background signal contributed by the plate, buffer, and other non-reactant pieces of the reaction system and chemistry can be identified. The raw emission data can be normalized by dividing the emission data by the identified baseline signal. According to various embodiments, the normalized amplification profile can normalize to an initial value of 1, because the actual signal emerges from the baseline at the point exponential growth begins. A normalized amplification profile based on a ratio to the baseline can create a more uniformly scaled amplification curve across different samples, filters, wells, dyes, or machines.

7 Claims, 4 Drawing Sheets

OTHER PUBLICATIONS

U.S. Appl. No. 12/022,098 Office Action dated Mar. 16, 2009, 9 pgs.
U.S. Appl. No. 12/022,094 Office Action dated Feb. 3, 2009, 16 pgs.
U.S. Appl. No. 12/022,079 Response to Office Action dated Nov. 17, 2009 filed May 14, 2010, 5 pgs.

* cited by examiner

SYSTEMS AND METHODS FOR BASELINE CORRECTION USING NON-LINEAR NORMALIZATION

RELATED APPLICATION

This application claims priority to U.S. Provisional Patent Application No. 60/898,064, filed Jan. 29, 2007, entitled "Systems and Methods for Optical and Spectral Calibration of Real-Time PCR Instrumentation," which is incorporated herein in its entirety.

BACKGROUND

Real-time polymerase chain reaction (RT-PCR) technology, as presently practiced, relies upon the accurate detection of fluorescent emission signals above an initial baseline. The baseline signal can represent a combination of spurious or unwanted signal contributions such as the residual fluorescence contributed by the plastic or other material of a sample plate, the fluorescence of a running buffer or other non-reactant liquid material, noise in the optical detector or detection electronics, or some other source of background signal noise or detection floor that is not a product of the amplification or other reaction. In various known RT-PCR implementations, better accuracy in the detection of the amplification signal, and hence original sample quantity, is frequently sought by characterizing the baseline floor over the first few PCR cycles, or pre-signal detection cycles, and then subtracting the baseline from the detected emissions once an inflection point into the exponential region has been reached. In general, a RT-PCR emission or other amplification graph, chart, or profile typically displays three sections or regions: an initial baseline region, an exponential region, and a plateau region. An example of this is shown in the illustration in FIG. 1. The baseline region can display a linear, or approximately linear, or other form over the first several cycles, as reaction chemistries have not liberated enough marker dye to rise over the detected background. The next, exponential region represents the rise of amplification product over the noise or background floor, as the PCR reaction kinetics come into force. The plateau region typically exhibits a final flattening or tapering of detected emission intensities, as reagents are exhausted. The combined amplification profile usually resembles a sigmoid or S-shape. Typically, RT-PCR systems determine a threshold cycle ($C_T$) which represents the cycle point at which the exponential threshold is reached. From that parameter the original sample quantity can be back-calculated, using standard curves.

Known baselining techniques involve the adjustment or normalization of the detected emission signal by subtracting the identified baseline in the first few cycles from the detected fluorescent intensities of the RT-PCR marker dyes in later cycles, to sharpen the accuracy of the absolute value of detected emission data in the exponential and/or plateau regions of the amplification profile. Baselining that relies upon a subtraction operation to perform normalization can, however, cause certain effects in the resulting modified or normalized data. For one, if a baselining operation is performed on a per-filter or per-dye wavelength basis, the baselining operation can determine different baselines for different filters or dyes, which after subtraction from the emission data lead to differing results for different detected channels. For another, if individual wells of a sample plate or other support or container are individually processed to create separate baselines on a per-well basis, the set of resulting baselined signals can be at a different scale or level. Furthermore, known baselining techniques involve the initial computation of baseline levels over the first few cycles, before exponential or plateau-region reactions takes place. Subtracting those baseline levels from a set of exponential or plateau-region data captured at a later point can introduce inaccuracies, for instance if the baseline level drifts over later cycles. A need exists for baseline and related techniques that address these and other issues.

SUMMARY

Systems and methods according to various embodiments of the present teachings relate to techniques and platforms to capture, identify, and characterize the baseline level of detected emission data of an amplification reaction, and to normalize the detected intensity data in an identified exponential region, plateau region, or other region of the detected data. According to various embodiments, the adjustment or normalization of the emission data can be performed by dividing the raw detected emission signal by the identified baseline, resulting in a normalized, scaled, or weighted representation of the emission signal. According to various embodiments, because each normalized signal can increase from a normalized background level of unity or close to unity (since the initial amplification cycles show a detected signal equal to the background or baseline signal), a uniform or consistent scale can be created across different dyes, filters, wells, or plates. According to various embodiments, the division of the detected signal by the identified baseline can be performed in real-time, so that the resulting adjusted or normalized signal is output as the RT-PCR operation or other analysis takes place.

FIGURES

DESCRIPTION

Figure 1:
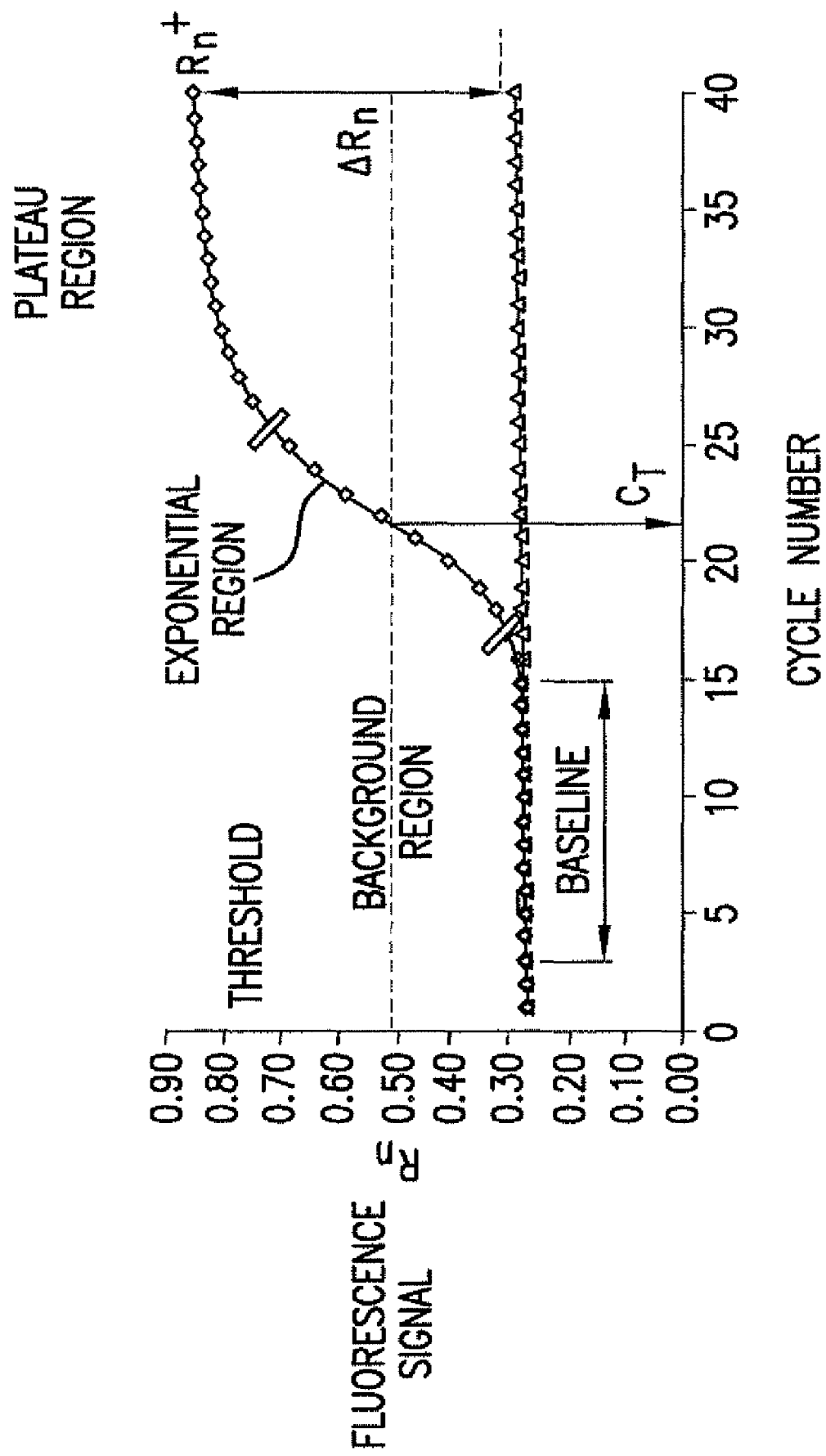
FIG. 1 illustrates an exemplary PCR amplification profile or curve, according to various embodiments of the present teachings.

Various embodiments of the present teachings relate to systems and methods for baseline correction or adjustment of RT-PCR or other amplification curves, signatures, graphs, profiles, or data, using a non-linear or non-subtractive normalization process. According to various embodiments, an amplification curve, signature, graph, profile, or data can be received from detection of fluorescent emissions in a RT-PCR or other instrument. According to various embodiments, the calibration systems and methods can be implemented in or applied to RT-PCR scanning systems or RT-PCR imaging systems, or other systems or platforms. In some embodiments, systems and methods according to the present teachings can be applied to non-real-time PCR instruments.

According to various embodiments, RT-PCR or other processing can take place using a standard sample plate, such as a 96-well or other capacity microtitre well or plate. In some embodiments, each well or other container or location in a plate or other platform can contain samples, for example, samples of DNA fragments or other material, to which one or more spectrally distinct dye is attached for detection and analysis. According to various embodiments, a calibration, normalization, or other adjustment can be performed to normalize, adjust, or otherwise increase the consistency and/or accuracy of the readings taken from the sample wells. According to various embodiments, the normalization or calibration can correct or compensate for variations due to or affected by factors which include, for example, differences in signal strength, dye or sample concentrations, contaminations, spectral or amplitude distortions, deviations in optical path, plate geometry, fluorescent noise floor, sample population or size, or other variations or anomalies that can arise from dye-to-dye, well-to-well, plate-to-plate, or instrument-to-instrument variations.

According to various embodiments, the normalization or calibration can comprise adjusting detected emission signals to compensate for identified background or baseline signal or signals in a RT-PCR amplification, or other reaction. According to various embodiments, this can permit correction or adjustment for background optical uniformity, utilizing a normalized amplification profile, signature, graph, curve, or data, based upon the baseline of the detected PCR or other readings. According to various embodiments, the normalization can be carried out using an endpoint of the PCR emission data, in addition to, or instead of, the initial baseline. According to various embodiments, calibration or normalization can be conducted in real-time, as the emission data from the PCR or other amplification or other process is detected. Herein, the term "emission" is used to exemplify a signal detected and/or calibrated according to various embodiments of the present teachings. It is to be understood that by "emission" the present teachings are referring to not only electromagnetic radiation but rather are also referring to any physical or chemical signal or other data that can be read, detected, imaged, or surmised from one or more area of interest, for example, a support region such as a well of a multi-well plate. "Emission" herein is intended to encompass electromagnetic radiation, optical signals, chemiluminescent signals, fluorescent signals, radiation transmission values, and radiation absorption values.

According to various embodiments, a background reading can be taken with no dyes, samples, background samples, or other material present in the sample plate or other support. In some embodiments, a background sample is used that comprises the same PCR mixture as is used on actual runs, but without the dyes. The background sample can mimic the actual run time background. For example, the background emission of a plate having dry or empty wells can be detected to determine baseline signal or signals caused by residual fluorescent contributions from the material of the plate itself, for example, from plastic or other material. Knowledge of the dry-plate contribution can also be used to determine if any other factors are contributing to the noise floor or detectable background which can be present in the system, or to quantify that remaining contribution.

Figure 2:
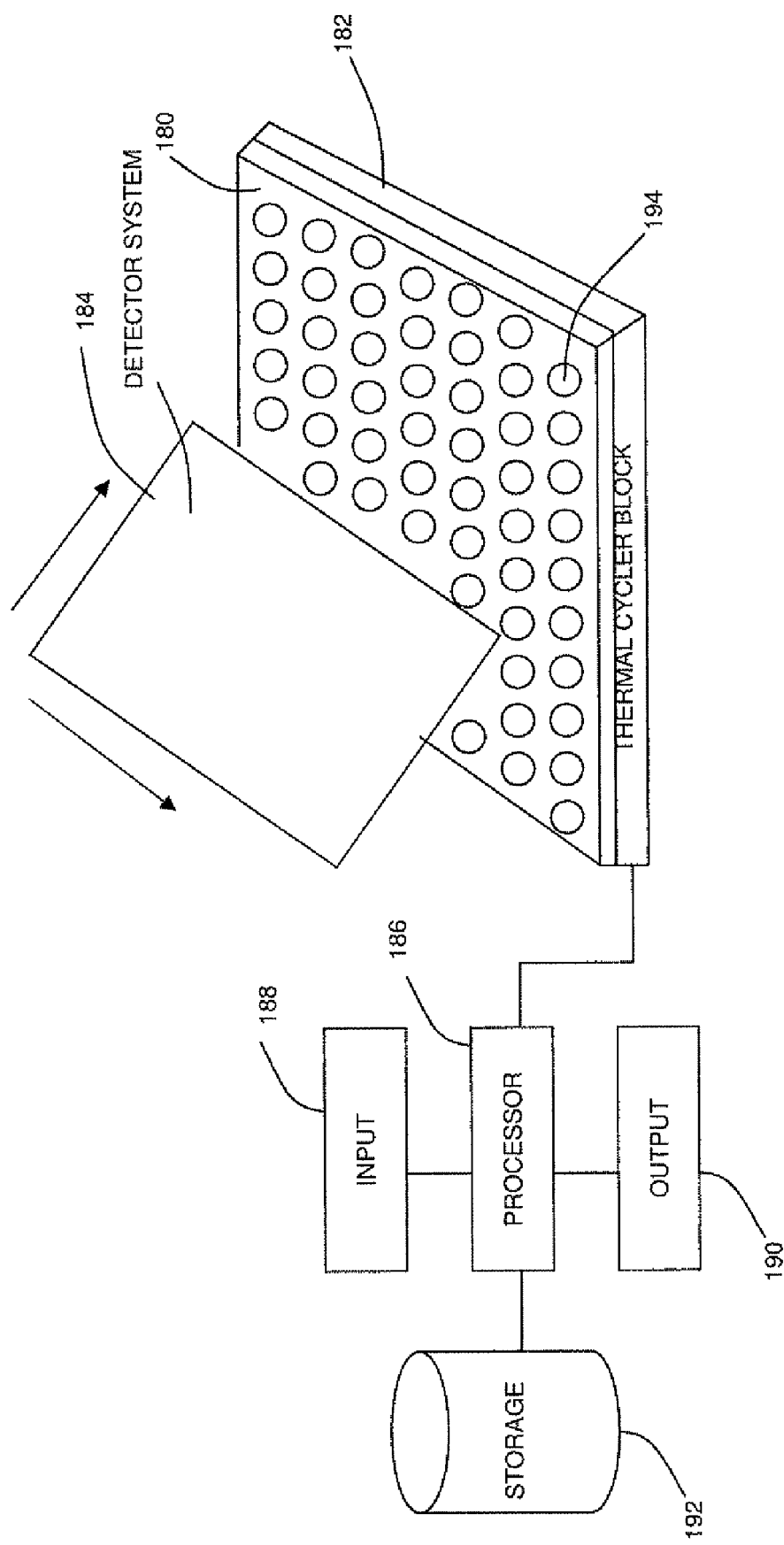
FIG. 2 illustrates a schematic of a PCR detection system, according to various embodiments of the present teachings.

According to various embodiments, background normalization and correction can be performed in connection with a RT-PCR system, such as, for instance, an overall system schematically illustrated in FIG. 2. According to embodiments as shown, a RT-PCR system can comprises a detector system 184, such as a scanning or whole-plate imaging optical detection element which can comprise, for example, a photomultiplier tube, CCD device, or other optical or other detection element. According to various embodiments, the detector system 184 can communicate with a processor 186 which can communicate with an input module 188, an output module 190, and/or storage 192, such as local or networked disk storage. According to various embodiments, the detector system 184 can scan or image a sample plate 180, to detect the optical emission from a set of sample wells 194, such as wells arranged in a standard 96, 384, or other capacity array. According to various embodiments, sample wells 194 can contain samples in mixture with reagents to conduct a RT-PCR run. In some embodiments, the RT-PCR processing can comprise operating the system at a series of RT-PCR temperatures regulated by thermal cycler block 182 and other electronic and thermal components, to subject the reactants in sample wells 194 to a desired sequence of denaturing, annealing, extension, and other steps.

Figure 3:
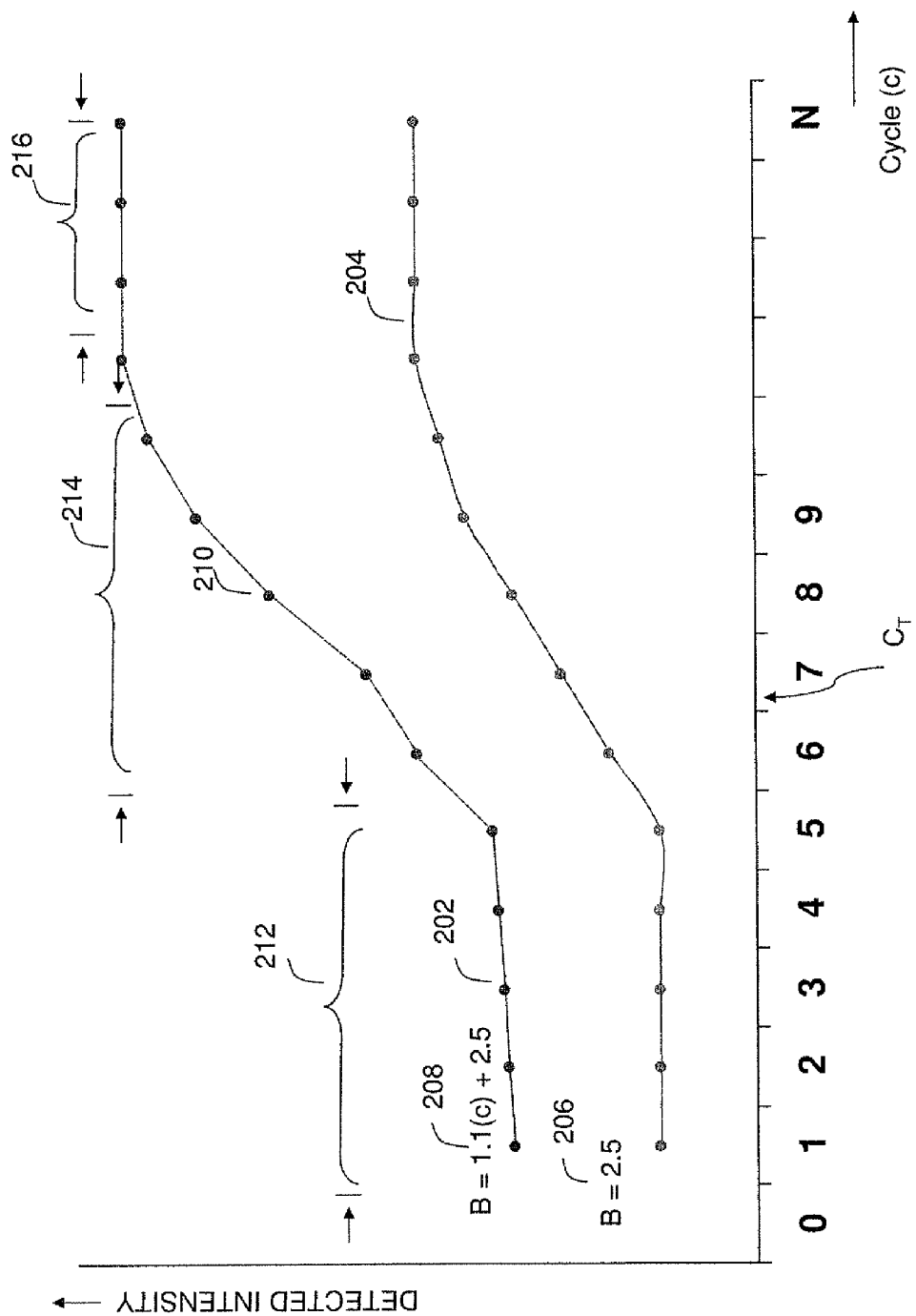
FIG. 3 illustrates a normalized or adjusted PCR amplification profile or curve, according to various embodiments of the present teachings.

According to various embodiments, and as illustrated, for instance, in FIG. 3, the output of a RT-PCR run can comprise a set of detected emission data 210, generally representing detecting intensities of fluorescent or other markers identifying PCR amplification products. According to various embodiments, emission data 210 can comprise discrete values. In some embodiments, emission data 210 can comprise discrete values that are interpolated, re-sampled or oversampled, to produce a more dense, or differently-spaced, collection of data points. In some embodiments, emission data 210 can comprise a continuous curve or trace. According to various embodiments, emission data can extend over a total number of cycles from 1 to N, where N can be the endpoint of a RT-PCR run, such as 30, 35, 40, or another number of cycles. According to various embodiments, the horizontal axis of the illustrative emission signature or profile shown in FIG. 3 can comprise cycle numbers, or it can comprise time units. According to various embodiments, the vertical axis can comprise absolute or relative amplitude or intensity units, or other measures. In some embodiments, the vertical axis can, for example, reflect detected emission or intensity values a on a logarithmic scale.

According to various embodiments, the baseline correction can comprise the amplitude readings detected and received in the first few cycles of a RT-PCR or other reaction, to isolate the initial cycles in which amplification product is not yet detectable. According to various embodiments, in the context of RT-PCR processes, the beginning and end cycles, which can form a candidate interval for defining the baseline region, can be on the order of cycles 1 through 8, respectively, or lower or higher cycles. According to various embodiments, mathematical tests can be applied to the detected signal in the first several cycles of RT-PCR operation to determine the baseline region 212, such as determining a set of cycles over which the first derivative of the detected signal remains below a predetermined threshold, or some other threshold. According to various embodiments, techniques such as those described in U.S. Pat. No. 7,228,237 to Woo et al., which is incorporated herein in its entirety by reference, or others, can be used to isolate and identify the baseline region 212 and baseline signal 202 located in the baseline region 212 of emission data 210.

According to various embodiments of the present teachings in one regard, and as, for example, also illustrated in FIG. 3, once the interval of baseline region 212 is identified and baseline signal 202 isolated, further normalization or adjustment of emission data 210 located in the remaining regions of emission data 210 can be performed. According to various embodiments in one regard, the normalization or other adjustment can comprise a division of the detected RT-PCR or other emission data 210 in exponential region 214 (and/or plateau region 216) by the detected baseline signal 202. According to various embodiments, this can generate a normalized amplification profile 204 in which the detected emission signals in exponential region 214 and/or plateau region 216 are scaled, normalized, or otherwise adjusted to represent the ratio of the detected signal in the respective region to the baseline signal 202. According to various embodiments, baseline signal 202 can comprise a constant, non-varying, or scalar value. According to various embodiments, normalized amplification profile 204 can be generated by dividing emission data 210 with constant 206, where baseline signal 202 is determined to be a scalar or constant value.

According to various embodiments, baseline signal 202 can be represented, encoded, or characterized by a time-varying function 208. According to various embodiments, function 208 can be or include a linear function, for instance, a linear function generated by performing a least-squares or other fitting operation on the data points in the first several cycles of the emission data. According to various embodiments, function 208 can be or include a non-linear function, such as a polynomial or other function. According to various embodiments, the division of the detected emission signals in exponential region 214 (and/or plateau region 216) by baseline signal 202, which is characterized by a function 208, can produce normalized amplification profile 204 reflecting that ratio of functions. According to various embodiments, the raw emission data 210, the baseline signal 202, the normalized amplification profile 204, and other signals can each be a continuous graph, function, or data set, or can be a discrete graph, function, or data set. According to various embodiments, normalization generated by computing a ratio of emission data 210 over function 208 can produce a normalized amplification profile 204, whose degree of scaling varies along the cycle number (or time) axis, depending upon the varying values of baseline signal 202 along that axis.

According to various embodiments, the normalized amplification profile 204 can provide a compactly-scaled representation of the underlying emission data when compared to the subtraction of a baseline value, since division of the emission data 210 by function 208 can reduce the overall normalized range. According to various embodiments, normalized amplification profile 204 can in one regard represent a more consistent basis upon which to compare or calibrate different RT-PCR or other runs, because the dynamic range of each is expressed in terms of a ratio over baseline.

According to various embodiments, the division of the detected emission data 210 from RT-PCR or other sources by baseline signal 202, in either the form of constant 206 or function 208, can be performed in real-time, while emission data 210 are being detected, collected, and stored. According to various embodiments, the division or other normalization operation giving rise to normalized amplification profile 204 can be performed after emission data 210 has been collected. According to various embodiments, the correction for baseline signal noise can also include other mathematical functions, treatments, computations or operations, in addition to generating a ratio of emission data 210 over baseline signal 202.

According to various embodiments, for example, after normalization by division of emission data 210 by baseline signal 202 as described herein, normalized amplification profile 204 can be further normalized or adjusted by, for example, subtracting a constant value, such as 1 or some other value, from normalized amplification profile 204. According to various embodiments, at the point that the detected emission data 210 first rises above baseline signal 202, the ratio of those two quantities can be 1 or substantially close to 1. Subtracting 1 or some other offset, from the ratio initially generated by normalized amplification profile 204, can result in an overall amplification profile with detected values increasing from a level of zero. According to various embodiments, other further or alternative adjustments to normalized amplification profile 204 can be made. According to various embodiments in one regard, because the normalized amplification profile 204 can be consistently scaled to starting points of 0, 1, or other desired levels, comparison, averaging, and other aggregate manipulation of the profiles generated by different wells, filters, dyes, samples, machines, or other entities, can be uniformly performed. Therefore, a set of multiple normalized amplification profiles generated according to the present teachings can be employed to generate more useful and accurate comparisons, make uniformity corrections, and other calibration or operational measurements, between diverse machines, chemistries, or processes.

Figure 4:
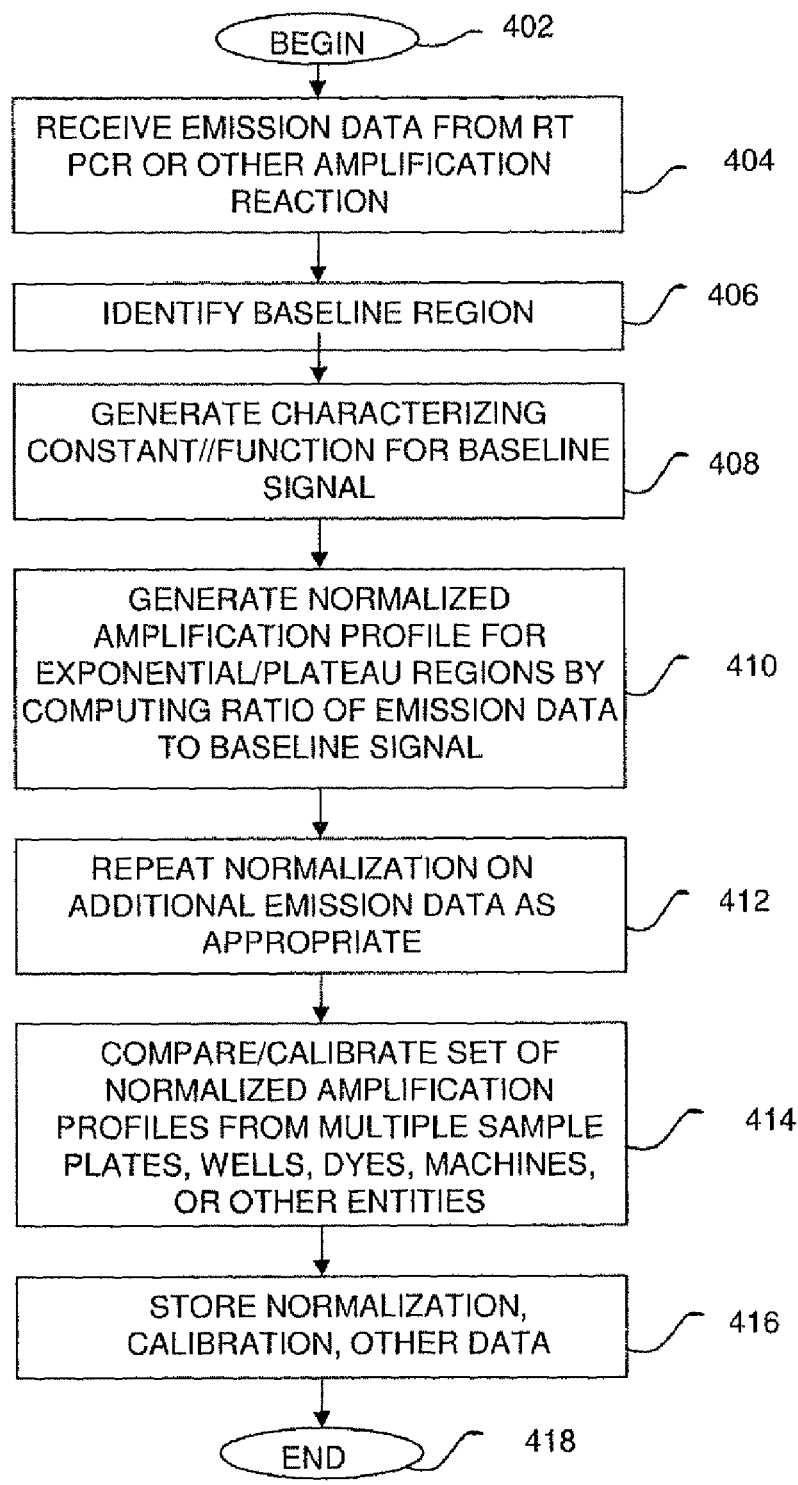
FIG. 4 illustrates a flowchart of baseline processing, according to various embodiments of the present teachings.

FIG. 4 illustrates a flowchart of overall baseline and emission normalization processing, according to various embodiments of the present teachings. In step 402, processing can begin. In step 404, emission data 210 from a RT-PCR or other amplification, or other machine, instrument, or system can be detected or received. In step 406, a baseline region 212 in the emission data 210 can be identified, for instance, based, for example, upon the greatest first derivative point or other technique. In step 408, a constant 206 and/or function 208 characterizing baseline signal 202 can be generated. In step 410, a normalized amplification profile 204 can be generated for the exponential region 214 and/or plateau region 216 of emission data 210. According to various embodiments, the normalized amplification profile 204 can be generated by dividing emission data 210 by constant 206, function 208, a combination of the two, or some other quantity or parameter. In step 412, additional sets of emission data 210, for example, emission intensities detected in additional RT-PCR or other runs, can be normalized using the same techniques.

In step 414, the set of one or more normalized amplification profile 204 can be compared, calibrated, or otherwise processed, for example, to perform uniformity calibration or analysis across different sample plates, wells, dyes, samples, filters, machines, or other entities. In step 416, any one or more normalized amplification profile 204, emission data 210, constant 206, function 208, or other data or information can be stored, for example, to a local hard disk, network storage site, or other location or data store. In step 418, processing can repeat, return to a prior processing point, proceed to a further processing point, or end.

Various embodiments of the present teachings can be implemented, in whole or part, in digital electronic circuitry, or in computer hardware, firmware, software, or in combinations thereof. Apparatus of the invention can be implemented in a computer program, software, code, or algorithm embodied in machine-readable media, such as electronic memory, CD-ROM or DVD discs, hard drives, or other storage device or media, for execution by a programmable processor. Various method steps according to the present teachings can be performed by a programmable processor executing a program of instructions to perform functions and processes according to the present teachings, by operating on input data and generating output. The present teachings can, for example, be implemented in one or more computer programs that are executable on a programmable system including at least one programmable processor coupled to receive data and instructions from, and to transmit data and instructions to, a data storage system or memory, at least one input device such as a keyboard and mouse, and at least one output device, such as, for example, a display or printer. Each computer program, algorithm, software, or code can be implemented in a high-level procedural or object-oriented programming language, or in assembly, machine, or other low-level language if desired. According to various embodiments, the code or language can be a compiled, interpreted, or otherwise processed for execution.

Various processes, methods, techniques, and algorithms can be executed on processors that can include, by way of example, both general and special purpose microprocessors, such as, for example, general-purpose microprocessors such as those manufactured by Intel Corp. or AMD Inc., digital signal processors, programmable controllers, or other processors or devices. According to various embodiments, generally a processor will receive instructions and data from a read-only memory and/or a random access memory. According to various embodiments, a computer implementing one or more aspects of the present teachings can generally include one or more mass storage devices for storing data files, such as magnetic disks, such as internal hard disks and removable disks, magneto-optical disks, and CD-ROM DVD, Blu-Ray, or other optical disks or media.

According to various embodiments, memory or storage devices suitable for storing, encoding, or embodying computer program instructions or software and data can include, for instance, all forms of volatile and non-volatile memory, including for example semiconductor memory devices, such as random access memory, electronically programmable memory (EPROM), electronically erasable programmable memory, EEPROM, and flash memory devices, as well as magnetic disks such as internal hard disks and removable disks, magneto-optical disks, and optical disks. Any of the foregoing can be supplemented by, or incorporated in, ASICs. According to various embodiments, processors, workstations, personal computers, storage arrays, servers, and other computer, information, or communication resources used to implement features of the present teachings can be networked or network-accessible.

It will be appreciated that while various embodiments described above involve the calibration of one or more aspects of instrument reading, dye selection or preparation, or other factors, according to various embodiments, more than one type of normalization or calibration can be performed, together or in sequence. While the foregoing description has generally described the normalization of the emission data as involving generating a ratio of data to a baseline signal according to various embodiments, the normalization can comprise, for example, dividing the emission data in the exponential region 214 and/or plateau region 216 by the endpoint value of the RT-PCR run, after the amplification reaction is complete.

Other embodiments will be apparent to those skilled in the art from consideration of the present specification and practice of the present teachings disclosed herein. It is intended that the present specification and examples be considered as exemplary only.

What is claimed is:

1. A system for generating a normalized amplification profile, comprising:
    an input unit, the input unit configured to receive emission data detected in an amplification reaction; and
    a processor, communicating with the input unit, the processor being configured to
        identify a baseline signal in the emission data,
        generate a normalization quantity by dividing the emission data by the identified baseline signal,
        generate the normalized amplification profile based on a ratio of the emission data to the normalization quantity,
        generate a threshold cycle ($C_T$) based on the normalized amplification profile, and
        quantify an original sample amount based on the threshold cycle ($C_T$).

2. The system of claim 1, wherein identifying a baseline signal comprises identifying a baseline signal based on a derivative of the emission data.

3. The system of claim 1, wherein the processor is further configured to subtract an offset from the normalized amplification profile.

4. The system of claim 1, wherein the processor is further configured to generate a plurality of normalized amplification profiles.

5. A computer program product for executing a method of generating a normalized amplification profile, tangibly stored on a non-transitory computer-readable medium, comprising instruction operable to cause a programmable processor to execute the method comprising:
    receiving emission data detected in an amplification reaction;
    identifying a baseline signal in the emission data;
    generating a normalization quantity by dividing the emission data by the identified baseline signal;
    generating the normalized amplification profile based on a ratio of the emission data to the normalization quantity;
    generating a threshold cycle ($C_T$) based on the normalized amplification profile; and
    quantifying an original sample amount based on the threshold cycle ($C_T$).

6. The computer program product of claim 5, wherein the method further comprises subtracting an offset from the normalized amplification profile.

7. The computer program product of claim 5, wherein the method further comprises generating a plurality of normalized amplification profiles, and performing a uniformity calibration based on the plurality of normalized amplification profiles.

* * * * *